United States Patent
Heck et al.

(10) Patent No.: US 9,468,659 B2
(45) Date of Patent: Oct. 18, 2016

(54) **NUTRACEUTICAL SUPPLEMENT WITH *LACTOBACILLUS RHAMNOSUS***

(71) Applicant: NWO Stem Cure, LLC, Findlay, OH (US)

(72) Inventors: Bruce E. Heck, Alvada, OH (US); Dong Hyun Kim, Sylvania, OH (US)

(73) Assignee: NWO STEM CURE, LLC, Findlay, OH (US)

( * ) Notice: Subject to any disclaimer, the term of this patent is extended or adjusted under 35 U.S.C. 154(b) by 49 days.

(21) Appl. No.: 14/534,745

(22) Filed: Nov. 6, 2014

(65) Prior Publication Data

US 2016/0129056 A1 May 12, 2016

(51) Int. Cl.
| | |
|---|---|
| A61K 35/747 | (2015.01) |
| A61K 31/593 | (2006.01) |
| A61K 36/296 | (2006.01) |
| A61K 36/324 | (2006.01) |
| A61K 36/82 | (2006.01) |
| A61K 36/9066 | (2006.01) |
| A61K 36/9068 | (2006.01) |
| A61K 31/12 | (2006.01) |
| A61K 31/00 | (2006.01) |
| A61K 35/00 | (2006.01) |

(52) U.S. Cl.
CPC ............ *A61K 35/747* (2013.01); *A61K 31/00* (2013.01); *A61K 31/12* (2013.01); *A61K 31/593* (2013.01); *A61K 36/296* (2013.01); *A61K 36/324* (2013.01); *A61K 36/82* (2013.01); *A61K 36/9066* (2013.01); *A61K 36/9068* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 8,734,855 B2 | 5/2014 | Liu et al. | |
| 2004/0013656 A1* | 1/2004 | Matsubara | A23C 11/106 424/93.45 |
| 2004/0208863 A1* | 10/2004 | Versalovic | A61K 35/744 424/115 |
| 2006/0112584 A1 | 6/2006 | Jones | |
| 2007/0154575 A1 | 7/2007 | Shimoda et al. | |
| 2008/0020018 A1 | 1/2008 | Moodley et al. | |
| 2008/0113031 A1 | 5/2008 | Moodley et al. | |
| 2008/0220084 A1* | 9/2008 | Fan | A61K 36/00 424/538 |
| 2013/0171117 A1* | 7/2013 | Grompone | A61K 35/74 424/93.45 |

FOREIGN PATENT DOCUMENTS

| | | |
|---|---|---|
| CA | 2481486 A1 | 10/2003 |
| CA | 2580591 A1 | 9/2007 |
| DE | 102008056312 A1 | 5/2010 |
| WO | 03021515 A2 | 3/2003 |
| WO | 2010051792 A1 | 5/2010 |
| WO | 2014083438 A2 | 6/2014 |

* cited by examiner

*Primary Examiner* — Allison Fox
(74) *Attorney, Agent, or Firm* — Fraser Clemens Martin & Miller LLC; Jacob M. Ward

(57) ABSTRACT

Compositions and uses thereof include an admixture of a probiotic and natural phytochemicals that can affect an individual's stem cells and the inflammatory process to reduce underlying symptoms of various health issues, including arthritis, aging, and physical or athletic injuries, thereby facilitating healing and repair of tissues.

19 Claims, No Drawings

NUTRACEUTICAL SUPPLEMENT WITH *LACTOBACILLUS RHAMNOSUS*

FIELD

The present technology relates to compositions and uses thereof to aid joint support, aging, and sports medicine recovery and performance that include *Lactobacillus rhamnosus*.

BACKGROUND

This section provides background information related to the present disclosure which is not necessarily prior art.

Treatment of various musculoskeletal disorders and injuries is an ongoing problem. The body's joints, ligaments, muscles, nerves, tendons, and structures that support the limbs, neck, and back can be afflicted by degenerative diseases and inflammatory conditions that cause pain and impair normal activities. The body can also suffer injuries from strenuous activities, repetitive activities, or accidents that include abrasions, contusions, and fractures. Certain musculoskeletal issues arise from arthritis, aging, and participation in various physical or athletic activities.

Arthritis, for example, is a common disease resulting in inflammation that breaks down the lining of joints and cartilage. Osteoarthritis is the most common form of arthritis. It is the result of aging "wear and tear" and trauma to the joint, such as sports injuries or fractures. Major complaints of individuals with arthritis include joint pain, swelling, warmth, weakness, giving way of joint, instability, catching, popping, stiffness, poor sleep, muscle pain and fatigue. Autoimmune arthritides, such as rheumatoid arthritis, occurs when the body's immune system attacks itself. Osteoarthritis and rheumatoid arthritis are characterized by joint inflammation and cartilage degradation. Mesenchymal stem cells can rebuild cartilage, where the stem cells are resident in the superficial zone of articular cartilage. Treatment of arthritis has relied on relieving symptoms by exercise, braces, weight loss, medications, and surgery including total joint replacement. Medications such as non-steroidal anti-inflammatory drugs (NSAIDs) have risks that include the stomach, cardiovascular system and kidneys leading to ulcers, heart attacks and kidney failure. There is no disease modifying treatment for osteoarthritis. Osteoarthritis is accelerated with obesity/weight gain due to increased joint reactive forces.

Aging is a course of degeneration that is associated with the onset of many diseases. As people age, the prevalence of conditions associated with systemic inflammation, such as obesity, increases which is a common manifestation of aging. The body's ability to stimulate new bone marrow cells including mesenchymal stem cells decreases during aging, the result of which weakens the immune system and the ability to regenerate tissues. Conditions currently identified with an increased prevalence with age and increased inflammation include osteoarthritis, rheumatoid arthritis, cardiovascular disease, diabetes, obesity, Alzheimer's, chronic kidney disease, autoimmune disease, cancer, and other diseases. Symptoms of aging are associated with the underlying oxidative stress, increased inflammation, weakened immune system and the body's decreased ability to form new cells and tissues. Major symptoms of aging include fatigue, lethargy, changes in sleeping pattern, poor memory, poor vision, wrinkles, poor dentition, sexual dysfunction, decreased libido, type II diabetes, increased weight gain, fractures, constipation, skin changes including brown spots, loss of skin elasticity, menopause, hearing loss, increased bone fracture, arthritis, to name a few.

Injuries resulting from physical and athletic activities include muscle strains, joint sprains, ligament injuries, cartilage injuries, fractures and overuse conditions. Joints that are often attended to by an orthopedic surgeon for sports injury include the shoulder, knee, ankle, elbow, and wrist. Sports injuries can be accompanied by symptoms including pain, stiffness, swelling, feelings of instability, weakness, redness, crepitance, bruising, and/or mechanical symptoms such as locking or catching in a joint. Sports medicine has developed as a specialty for the prevention and treatment of sports-related injuries that occur at the ligament, muscle, tendon, and bone. Conventional treatment for sports injuries includes rest, ice, compression, elevation. Additional treatments include physical therapy and sports medicine rehabilitation, medication such as NSAIDs to reduce inflammation that exacerbates the injury and leads to surgery. There is no known medication or current treatment to accelerate the healing process after injury. Aging athletes are at increased risk of sports injury. An overweight, obese athlete is less physically fit and at increased risk of injury including arthritis due to increased joint reactive forces.

Mitigation of one or more symptoms or issues arising from joint problems, aging, and sports related injuries often includes the use of various anti-inflammatory treatments. Current anti-inflammatory treatments exhibit certain limitations. For example, the most commonly prescribed inflammatory/arthritis medications are the various NSAID drugs. NSAIDs include over the counter products, such as ibuprofen, acetaminophen, naproxen, and aspirin, and also include prescription formulations that of naproxen and celecoxib. Several of these medications are associated with one or more side effects, some of which can be severe. Acetaminophen-associated overdoses, in particular, account for about 56,000 emergency room visits and about 26,000 hospitalizations yearly and more than 450 deaths from liver failure. Acetaminophen is also the number one cause of acute liver failure and can result in kidney toxicity. NSAIDs can further induce nausea, heartburn, ingestion, abdominal pain, bleeding ulcer (GI complaints), where approximately 16,500 people per year die as a result of NSAID-associated gastrointestinal complications and an estimated 107,000 patients are hospitalized annually for NSAID-related GI complications. NSAIDs can further present complications relating to heart attack, stroke (cardiovascular events), congestive heart failure, atrial fibrillation, and kidney damage.

It would be advantageous to have an alternative to NSAIDs for the treatment of various health issues including musculoskeletal disorders and injuries.

SUMMARY

In concordance with the instant disclosure, the present technology includes compositions and methods that relate to treatment of various health issues including musculoskeletal disorders and injuries.

In one embodiment, a dietary supplement is provided that includes *Lactobacillus rhamnosus*, ginger, and vitamin D, where the dietary supplement can be administered to aid a health issue related to one of joint support, aging, and sports medicine.

In another embodiment, a dietary supplement is provided that includes *Lactobacillus rhamnosus*, ginger, vitamin D, curcumin, and *Boswellia* extract, where the dietary supplement can be administered to provide joint support and mitigate one or more effects of arthritis.

In yet another embodiment, a dietary supplement is provided that includes *Lactobacillus rhamnosus*, ginger, vitamin D, *Boswellia* extract, and green tea extract, where the dietary supplement can be administered to mitigate one or more effects of aging.

In yet another embodiment, a dietary supplement is provided that includes *Lactobacillus rhamnosus*, ginger, vitamin D, curcumin, and *Epimedium* extract, where the dietary supplement can be administered to mitigate one or more effects arising from physical or athletic activities.

Further areas of applicability will become apparent from the description provided herein. The description and specific examples in this summary are intended for purposes of illustration only and are not intended to limit the scope of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments. Except where otherwise expressly indicated, all numerical quantities in this description are to be understood as modified by the word "about" in describing the broadest scope of the technology.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein. Additionally, it should be appreciated that all natural supplements disclosed herein may be provided in the synthetic form and used within the scope of the present disclosure.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

The present technology is drawn to compositions that include the probiotic organism *Lactobacillus rhamnosus* and methods of administering such compositions to aid various health issues, including joint support, aging, and sports medicine recovery and performance. In addition to *Lactobacillus rhamnosus*, the compositions can include a member selected from the group consisting of curcumin, *Boswellia* extract, ginger, vitamin D, green tea extract, *Epimedium* extract, and combinations thereof. Curcumin can be provided by tumeric or extracted therefrom. Additionally, it should be appreciated that curcumin may be provided in a synthetic form and used within the scope of the present disclosure. *Boswellia* extract can be obtained from *Boswellia serrata* (i.e., Indian Frankincense). Ginger can be obtained from the root of *Zingiber officinale*. Vitamin D can include cholecalciferol. Green tea extract can be obtained from *Camellia sinesnsis*. *Epimedium* extract can be obtained from *Epimedium sagittatum* (i.e., Horny Goat Extract). The compositions can be formulated for oral administration, including one or more tablets or capsules, liquid or slurry form, or as a powder or granulate. Other ingredients can be included, such as various excipients, including one or more antiadherents, binders, coatings, disintegrants, flavors, colors, lubricants, glidants, sorbents, preservatives, and sweeteners. Particular excipient examples include one or more of hypromellose, rice flour, magnesium stearate, cellulose, inulin, and silicon dioxide.

Various embodiments can provide compositions and uses thereof tailored to particular muscloskeletal disorders and/or injuries. In one embodiment, a composition for providing joint support and mitigating one or more effects of arthritis comprises *Lactobacillus rhamnosus*, vitamin D, curcumin, *Boswellia* extract, and ginger. The composition can be used to mitigate arthritic symptoms and pains, stimulate the generation of cartilage tissues from endogenous stem cells, and increase the body's antioxidant activity. In another embodiment, a composition for mitigating the effects of aging comprises *Lactobacillus rhamnosus*, *Boswellia* extract, ginger, green tea extract, and vitamin D. The composition can be used to provide a protective effect on cells and tissues against oxidative stress, decrease inflammation, and regulate the immune system. In yet another embodiment, a composition for mitigating issues arising from physical and athletic activities comprises *Lactobacillus rhamnosus*, curcumin, ginger, vitamin D, and *Epimedium* extract. The composition can be used to provide protection against oxidative stress, anti-inflammatory action, and immuno-modulatory effects. The various components used in the compositions are approved by the U.S. Food and Drug Administration (FDA) for human use as food and diet supplements and can present limited or no side effects, such as gastric irritation, stomach ulcers, hypertension, cardiovascular diseases, and kidney dysfunction.

*Lactobacillus rhamnosus* is approved by FDA for human use and can provide one or more activities attending to various health issues, including musculoskeletal issues. *Lactobacillus rhamnosus* can reduce the inflammatory symptoms of rheumatoid arthritis in humans. Oral ingestion of *Lactobacillus* can improve the Health Assessment Questionnaire (HAQ) score and reduce the levels of plasma inflammatory cytokines. *Lactobacillus rhamnosus* can ameliorate arthritis in animals Exopolysaccharide (EPS), the major component of *Lactobacillus rhamnosus*, has anti-arthritogenic properties. EPS or EPS-producing probiotics can suppress active arthritis. *Lactobacillus rhamnosus* can suppress inflammation in animals. *Lactobacillus rhamnosus* can reduce inflammatory signaling in immature intestines in animals. Thus, it can be expected to suppress intestinal inflammatory syndromes that present in newborns or children, such as necrotizing enterocolitis (NEC), idiopathic inflammatory bowel diseases (IBD), or infectious enteritis. *Lactobacillus rhamnosus* can reduce GI and respiratory infections. *Lactobacillus rhamnosus* can reduce the risk for gastrointestinal and respiratory tract infections in pediatric patients. Mice treated with *Lactobacillus rhamnosus* showed attenuated weight gain on a high fat diet (HD) (not normal diet [ND]) compared to those with PBS (P). Mice receiving *Lactobacillus rhamnosus* showed faster glucose clearance (higher insulin sensitivity) on HD. *Lactobacillus rhamnosus* can protect human colonic muscle. *Lactobacillus rhamnosus* can attenuate lipopolysaccharide (LPS)-caused inflammation that produces higher IL-6, lower IL-10 (anti-inflammatory) and can restore the contractility of muscle tissue and cells under inflammation. *Lactobacillus rhamnosus* can increase insulin sensitivity. *Lactobacillus rhamnosus* can reduce oxidative stress in athletes during intense exercise. Treatment with *Lactobacillus rhamnosus* can decrease the plasma levels of reactive oxygen metabolites (dROM) and biological antioxidant potential (BAP) in athletes who took intense exercise training. *Lactobacillus rhamnosus* can decrease the incidence of UV-induced tumor formation. Hairless mice treated with *Lactobacillus rhamnosus* showed a delay in tumor expansion in both number and size. *Lactobacillus rhamnosus* can enhance both natural and acquired immunity. Treatment with *Lactobacillus rhamnosus* can increase the plasma levels of peripheral leucocytes and peritoneal macrophages (phagocytic activities) and antibody, which suggests that *Lactobacillus rhamnosus* increases both innate and acquired immunity.

Accordingly, *Lactobacillus rhamnosus* provides several benefits, including the following. *Lactobacillus rhamnosus* is a unique probiotic strain. *Lactobacillus rhamnosus* can attenuate various types of arthritis. *Lactobacillus rhamnosus* functions as antioxidant which may make healthy cartilage cells. *Lactobacillus rhamnosus* can decrease the inflammatory cytokines that damage cartilage and joints. *Lactobacillus rhamnosus* can suppress the expression of inflammatory genes that cause pain and stiffness accompanied with arthritis. *Lactobacillus rhamnosus* can ameliorate rheumatoid arthritis. *Lactobacillus rhamnosus* can reduce oxidative stress and increases lifespan in the worm model, *C. elegan*. *Lactobacillus rhamnosus* can decrease inflammation. *Lactobacillus rhamnosus* can improve insulin-sensitivity and reduce fat accumulation. *Lactobacillus rhamnosus* can provide photoprotection against UV radiation. *Lactobacillus rhamnosus* shows anti-oxidant benefits in athletes during intense exercise training. *Lactobacillus rhamnosus* can decrease the risk of gastrointestinal and respiratory infections. *Lactobacillus rhamnosus* can reduce adiposity in animals on high fat diet. *Lactobacillus rhamnosus* can protect against UV-induced carcinogenesis. *Lactobacillus rhamnosus* is anti-inflammatory and immuno-modulatory.

Compositions including *Lactobacillus rhamnosus* and uses thereof can have various physical amounts of *Lactobacillus rhamnosus* and various amounts of colony forming units (CFU) of *Lactobacillus rhamnosus*. Examples include physical amounts ranging from 1 mg to 1000 mg, 10 mg to 500 mg, 50 mg to 100 mg, and 67 mg. Examples further include CFU values ranging from 100 million to 1 trillion, 1 billion to 100 billion, 5 billion to 50 billion, and 10 billion. Other amounts for the *Lactobacillus rhamnosus* may also be selected by one of ordinary skill in the art, as desired. These amounts can be provided and administered as a composition comprising a single dose or as multiple doses, can be provided as a single capsule or as multiple capsules, and can be admixed with other components, for example.

Curcumin is approved by FDA for human use and can provide one or more activities attending to various health issues, including musculoskeletal issues. As noted, curcumin can be provided by tumeric or extracted therefrom. Additionally, it should be appreciated that curcumin may be provided in a synthetic form and used within the scope of the present disclosure. Curcumin can have the same analgesic effect as ibuprofen in osteoarthritis patients. Curcumin can be as effective as ibuprofen for the treatment of knee osteoarthritis while it has fewer side effects than ibuprofen. Curcumin can suppress the activity of human synoviocytes that cause rheumatoid arthritis. Curcumin can suppress the production of inflammatory cytokines from synoviocytes that cause rheumatoid arthritis in patients. It can also suppress the expansion of human synoviocytes. Curcumin can suppress inflammation and arthritis in animals. Curcumin can suppress not only the production of inflammatory cytokines but also collagen-induced arthritis (CIA) in animals. Curcumin can enhance muscle regeneration after traumatic injury. Systemic treatment with curcumin can increase muscle mass (embryonic myosin heavy chain [EMHC]) and muscle cells in two different injured muscle sites (Masseter & tibialis anterior [TA]). Curcumin can increase cardiac muscle repair and can ameliorate cardiac failure. Curcumin can suppress the production of malondialdehyde (MDA [A]), a lipid peroxide, and matrix metalloproteases (MMPs) that damage cardiac muscle, in an animal model of myocardial infarction. Curcumin can suppress oxidative stress that causes muscle damage. Curcumin can suppress the production of oxidants (hydrogen peroxide & NADPH-oxidase) and muscle damage markers (MCP-1 & CXCL14) in the muscle of animals that underwent extensive exercise.

Accordingly, curcumin provides several benefits, including the following. Curcumin can be as safe and effective as an NSAID in the treatment of knee osteoarthritis. Curcumin can be anti-inflammatory. Curcumin can reduce inflammatory cytokines in cartilage. Curcumin can show an anti-arthritic effect in animals. Curcumin can promote cartilage formation from mesenchymal stem cells. Curcumin can reduce inflammation in the synovial lining of human joints. Curcumin can suppress collagen-induced arthritis in animals. Curcumin can show a therapeutic effect for the treatment of osteoarthritis. Curcumin can promote muscle repair. Curcumin may prevent loss of muscle mass and stimulate muscle regeneration after traumatic injury. Curcumin can reduce inflammation and can enhance eccentric exercise-induced muscle damage. Curcumin can promote cardiac repair. Curcumin can decrease oxidative stress following downhill running-induced muscle damage. Curcumin can have a therapeutic effect for the treatment of osteoarthritis.

Compositions including curcumin and uses thereof can employ various amounts. Examples include amounts ranging from 1 mg to 1000 mg, 10 mg to 700 mg, 100 mg to 500 mg, and 350 mg. Other amounts for the curcumin may also be selected by one of ordinary skill in the art, as desired. These amounts can be provided and administered as a composition comprising a single dose or as multiple doses, can be provided as a single capsule or as multiple capsules, and can be admixed with other components, for example.

Boswellia extract is approved by FDA for human use and can provide one or more activities attending to various health issues, including musculoskeletal issues. As noted, Boswellia extract can include Boswellia serrata extract. Boswellia extract can reduce osteoarthritis symptoms. Osteoarthritis patients who received Boswellia plant extract reported decreased knee pain and swelling, increased knee flexion, and increased walking distance. Boswellia plant extract reduced osteoarthritis-related pain and physical functions (visual analog scale), Lequesne's functional index, and WOMAC pain and stiffness. Boswellia extract can reduce arthritis and inflammation in animals. Boswellia extract can reduce arthritic scores, paw edema, and the local tissue pro-inflammatory cytokines tumor necrosis factor alpha (TNF-$\alpha$) and interleukin-1 beta (IL-1$\beta$) in a Lewis rat adjuvant arthritis animal model. Boswellia extract can restore memory in animals. Orally ingested Boswellia extract can reduce the escape latency and distance traveled but had no influence on swimming speed in the Morris water maze, suggesting that it enhances spatial memory in animals. Boswellia extract can have anti-tumor and anti-hyperlipidemic effects in animals. Orally ingested Boswellia plant extract can reduce TPA-induced skin inflammation and edema formation.

Accordingly, Boswellia extract provides several benefits, including the following. Boswellia Extract significantly improves pain score and physical function in osteoarthritis patients. Boswellia extract can suppress the activation of the inflammatory immune system. Boswellia extract can block cartilage matrix breakdown and can increase type II collagen and aggrecan in human osteoarthritis chondrocytes. Boswellia extract can reduce cartilage-degrading enzymes and inflammation in osteoarthritis patients. Boswellia extract can be anti-inflammatory, anti-arthritic, and analgesic. Boswellia extract can decrease knee pain and can increase knee flexion and walking distance. Boswellia extract can decrease joint inflammation and spinal arthritis. Boswellia Extract can improve memory in an aging animal model. Boswellia extract can have anti-oxidant and anti-thrombotic effects. Boswellia extract can increase the elasticity of photo-aged skin. Boswellia extract can exert anti-tumor and anti-hyperlipidemic effects.

Compositions including Boswellia extract and uses thereof can have various physical amounts of Boswellia extract and various amounts of boswellic acid. Examples include physical amounts ranging from 1 mg to 1000 mg, 10 mg to 800 mg, 100 mg to 600 mg, and 500 mg. Additionally, it should be appreciated that Boswellia extract may be provided in a synthetic form and used within the scope of the present disclosure. Other amounts for the Boswellia extract may also be selected by one of ordinary skill in the art, as desired. Examples further include where the physical amount includes various percentages of boswellic acid, including 1% to 100%, 10% to 90%, 25% to 75%, and 65%. These physical amounts and percentages can be provided and administered as a composition comprising a single dose or as multiple doses, can be provided as a single capsule or as multiple capsules, and can be admixed with other components, for example.

Ginger is approved by FDA for human use and can provide one or more activities attending to various health issues, including musculoskeletal issues. As noted, ginger can be obtained from the root of Zingiber officinale. Ginger can be as effective as an NSAID in reducing arthritic pain without gastropathy in patients. A ginger-containing supplement (Zinaxin) reduced arthritic pain (visual analogue scale [VAS]) to the same extent as diclofenac, an NSAID. Moreover, Zinaxin does not cause gastropathy that accompanies NSAID. Ginger can relieve osteoarthritis symptoms. Osteoarthritis patients treated with ginger showed a marked relief of osteoarthritis symptoms (based on Health Assessment Questionnaire) and progressing improvement without showing any sign of negative effects. Ginger can reduce inflammation and muscle soreness caused by exercise in patients. In 98 patients treated with ginger for 6 weeks, there was a significant decrease in muscle soreness and inflammation.

Accordingly, ginger provides several benefits, including the following. Ginger therapy can demonstrate a marked relief of osteoarthritis symptoms with few side effects. Ginger can suppress joint inflammation by reducing inflammatory cytokines in rheumatoid arthritis. Ginger can be as effective as the powerful steroid, betamethasone, in reducing osteoarthritis and rheumatoid arthritis. Ginger can reduce arthritis pain as much as diclofenac (NSAID) does in patients. Ginger can have antioxidant and protective effects against acetaminophen in animals. Ginger can have anti-oxidative, anti-inflammatory, anti-cancer, and anti-diabetic effects. Ginger can reduce muscle pain caused by exercise. Ginger can reduce muscle soreness caused by exercise. Long-term treatment with ginger can relieve osteoarthritis symptoms with few side effects.

Compositions including ginger and uses thereof can have various physical amounts of ginger where the physical amounts can include various concentration ratios. Examples include physical amounts ranging from 1 mg to 1000 mg, 10 mg to 800 mg, 100 mg to 600 mg, and 500 mg. Examples further include where the physical amount relates to a ginger concentrate range, including 1.5:1 to 20:1, 2:1 to 15:1, 5:1 to 10:1, and 8:1. Equivalent concentrations of gingeroles (active ingredients of ginger) may also be employed. Additionally, it should be appreciated that ginger may be provided in a synthetic form and used within the scope of the present disclosure. Other amounts for the ginger may also be selected by one of ordinary skill in the art, as desired. These amounts can be provided and administered as a composition comprising a single dose or as multiple doses, can be provided as a single capsule or as multiple capsules, and can be admixed with other components, for example.

Vitamin D is approved by FDA for human use and can provide one or more activities attending to various health issues, including musculoskeletal issues. As noted, vitamin D can include cholecalciferol. Vitamin D can decrease the effects of osteoarthritis in humans. Sunlight exposure and serum Vitamin D (25[OH]D) levels are positively correlated with a decrease in knee cartilage loss. Thus, achieving vitamin D sufficiency may prevent and/or retard cartilage loss in knee osteoarthritis. Vitamin D (1,25(OH)2D3) can reduce the arthritic production of matrix metalloprotease-9 and prostaglandin E2 (PGE2) in human articular chondrocytes. Vitamin D can increase proper bone formation and can decrease unwanted aortic calcification on a high phosphate diet. In chronic kidney disease, patients lose their production of proper bone-forming factors and gain unnecessary aortic calcification. Paricalcitol containing Vitamin D can reverse both. Vitamin D can increase bone formation. Vitamin D (1,25(OH)2D3) can increase the expression of protein factors (type I collagen, osteopontin, sialoprotein, osteocalcin, alkaline phosphatase, and BMP-2) that enhance bone formation.

Accordingly, vitamin D provides several benefits, including the following. Vitamin D levels are positively associated with improvement in knee cartilage volume. Vitamin D can suppress inflammation in osteoarthritis and rheumatoid arthritis. Vitamin D can exert anti-inflammatory action on synovial lining cells. Vitamin D levels can be associated with bone mineral density and protection of cartilage in osteoarthritic knee. Vitamin D-deficient athletes can have a smaller heart size. Vitamin D-deficiency can be associated with lower body mass in professional football players. Vitamin D directly affects skeletal muscle structure and function. Vitamin D can prevent overuse-caused injuries such as stress fracture. Vitamin D can modulate the age-related decline in muscle function and benefits the aging athlete. Vitamin D can be used for DNA repair, thus exerting an anti-aging effect. Vitamin D can have protective effects on cardiovascular disease, diabetes, auto-immune disease and cancer. Vitamin D can be important for anti-aging of the bone. Vitamin D can increase the expression of anti-aging genes. Vitamin D can induce bone formation in mesenchymal stem cells.

Compositions including vitamin D and uses thereof can have various amounts of vitamin D, including various ranges of international units (IU). Examples include IU values ranging from 1 IU to 10,000 IU, 10 IU to 7,500 IU, 100 IU to 5,000 IU, 500 IU to 2,000 IU, and 1,000 IU. Additionally, it should be appreciated that vitamin D may be provided in a synthetic form and used within the scope of the present disclosure. Other amounts for the vitamin D may also be selected by one of ordinary skill in the art, as desired. These amounts can be provided and administered as a composition comprising a single dose or as multiple doses, can be provided as a single capsule or as multiple capsules, and can be admixed with other components, for example.

Green tea extract is approved by FDA for human use and can provide one or more activities attending to various health issues, including musculoskeletal issues. As noted, green tea extract can be obtained from *Camellia sinesnsis* and can include various weight percentages of polyphenols, catechins, and epigallocatechin gallate (EGCG). Green tea extract can suppress skin damage and aging caused by UV light. Cream containing green tea extract can reduce UV-induced photo-aging and subsequent immunosuppression. Green tea extract can increase learning and memory in old rats. Both young and old rats treated with green tea extract showed shorter time to find a safe place (closed [dark] arm) and to take a proper avoiding action to a pain-inducing condition. Green tea extract can have bone-forming and anti-fat effects. Green tea extract can increase the activity of bone-forming alkaline phosphatase (ALP) and suppresses the proliferation of fat cells (adipocytes).

Accordingly, green tea extract provides several benefits, including the following. Green tea extract can be effective in enhancing learning and memory. Green tea extract can have bone-forming and anti-obesity effects. Green tea extract can have anti-oxidant and anti-aging effects. Green tea extract can have a UV protective effect. Green tea extract can protect blood cells from aging-induced oxidative stress.

Compositions including green tea extract and uses thereof can have various physical amounts of green tea extract and various amounts of polyphenols, catechins, and epigallocatechin gallate. Examples include physical amounts ranging from 1 mg to 1000 mg, 10 mg to 800 mg, 100 mg to 600 mg, and 500 mg. Examples further include where the physical amount includes polyphenols at 1% to 100%, 10% to 100%, 50% to 100%, and 98%. Examples further include where the physical amount includes catechins at 1% to 100%, 10% to 100%, 50% to 100%, and 80%. Examples further include where the physical amount includes epigallocatechin gallate at 1% to 100%, 10% to 90%, 25% to 75%, and 50%. Additionally, it should be appreciated that green tea extract may be provided in a synthetic form and used within the scope of the present disclosure. Other amounts for the green tea extract may also be selected by one of ordinary skill in the art, as desired. These amounts can be provided and administered as a composition comprising a single dose or as multiple doses, can be provided as a single capsule or as multiple capsules, and can be admixed with other components, for example.

*Epimedium* extract is approved by FDA for human use and can provide one or more activities attending to various health issues, including musculoskeletal issues. As noted *Epimedium* extract can be obtained from *Epimedium sagittatum* (i.e., Horny Goat Extract) and can have various weight percentages of icariin. *Epimedium* extract can increase the formation of bone cells. Treatment with *epimedium* extract increased the formation of bone cells from mesenchymal stem cells. *Epimedium* extract has a vaso-relaxant effect in animals. Icarrin, a major component of *epimedium* extract, can reduce blood pressure by relaxing coronary arterial vessel and increasing the activity of the antioxidant enzyme, eNOS, in the vessel. *Epimedium* extract can enhance peripheral nerve regeneration. *Epimedium* extract (Icarrin: major component) can promote peripheral nerve regeneration and improve the function of damaged nerves in a crush injury animal model. *Epimedium* extract can mimic one or more effects of testosterone. Icanin (ICA—a major component of *epimedium* extract) can increase the levels of circulating serum testosterone and serum bone Gla-protein (BGP), a marker of bone growth.

Accordingly, *Epimedium* extract provides several benefits, including the following. *Epimedium* extract can be a testosterone-mimetic. *Epimedium* extract can enhance the activities of the anti-oxidant enzymes, eNOS and NO. *Epimedium* extract can enhance the formation of bone cells from mesenchymal stem cells. *Epimedium* extract can improve bone formation and decrease bone absorption. *Epimedium* extract can have cardiovascular therapeutic effects. *Epimedium* extract can restore the function of damaged nerves and promote peripheral nerve regeneration.

Compositions including *Epimedium* extract and uses thereof can have various physical amounts of *Epimedium* extract with various weight percentages of icariin. Examples include physical amounts ranging from 1 mg to 1000 mg, 10 mg to 800 mg, 100 mg to 600 mg, and 500 mg. Examples further include where the physical amount includes various weight percentages of icariin, including 0.1% to 100%, 1% to 90%, 1% to 50%, 5% to 20%, and 10%. Additionally, it should be appreciated that *Epimedium* extract may be provided in a synthetic form and used within the scope of the present disclosure. Other amounts for the *Epimedium* extract may also be selected by one of ordinary skill in the art, as desired. These amounts can be provided and administered as a composition comprising a single dose or as multiple doses, can be provided as a single capsule or as multiple capsules, and can be admixed with other components, for example.

The compositions can be formulated in various ways, typically for oral administration. Examples include forming the compositions into various tablets or capsules, providing the compositions in a liquid or slurry form, or providing the compositions as powders or granulates. The composition components can be entirely admixed together into a single portion, each provided as a separate portion, or various components can be admixed where the whole composition is provided by more than one portion but where a total number of portions is less than the number of components. Other dosage forms suitable for oral administration can be used.

Other ingredients can be included in the present compositions, such as various excipients, including one or more antiadherents (e.g., magnesium stearate), binders (e.g., saccharides, gelatin, polymers), coatings (e.g., hydroxypropyl methylcellulose, enterics such as waxes, plastics, fibers etc.), disintegrants (e.g., polyvinylpyrrolidone, carboxymethyl cellulose, modified starches), flavors, colors, lubricants (e.g., talc, silica, fats), glidants (e.g., fumed silica, talc, magnesium carbonate), sorbents, preservatives (e.g., antioxidants such as vitamins A, E, and C), and sweeteners. Particular excipient examples include one or more of hypromellose, rice flour, magnesium stearate, cellulose, inulin, and silicon dioxide.

The present compositions and methods of administering such compositions can impact the way a body's stem cells respond to various health issues, including musculoskeletal issues. Stem cells include unique types of cells that have a remarkable potential to develop many different cell types. Stem cells can differentiate into other cell types, including fat, muscle, bone, cartilage, nerve, blood vessel, etc. They are important in early life during growth and repairing/replenishing tissues. Once a stem cell develops into specific cells, such as a fat cell, it typically can not form other tissues such as bone, cartilage, and muscle. The present compositions can impact stem cells and thereby reduce the inflammatory process and improve underlying symptoms. Keeping tissues healthy also leads to the possibility of disease modification and reducing symptoms/progression of health conditions.

Cells and tissues can be damaged with stress, lack of sleep, travel, certain medications, smoking, injury, aging, a poor diet, toxins, autoimmune diseases and many other causes. Stem cells can participate in the healing and repair of these damaged cells and tissues. Stem cells offer a renewable source of cells and tissues to treat multiple diseases, and conditions including arthritis, aging, and sports medicine injuries. Damaged cells and tissue can lead to accelerated aging and injury, including sports injuries. Currently, obesity is an epidemic resulting in stem cells forming more fat leading to lack of bone, cartilage, and blood vessels resulting in diabetes, hypertension, osteoporosis, arthritis, accelerated aging and sports medicine injuries.

The present compositions and uses thereof involve a paradigm shift in the thought of addressing the aging process. To slow the aging process, it is felt that keeping the cells that replenish the tissues (e.g., mesenchymal and hematopoietic stem cells) healthy is important. Aging declines the number of stem cells. Multiple scientific studies demonstrate the individual supplements in the present compositions can protect such cells. However, the combinations used in the present compositions revolutionize the current thought and approach to supporting joint health, anti-aging, and sports medicine performance/recovery. For example, without being bound by theory, it is believed that the present compositions and methods of using such compositions may direct a person's own stem cells to form muscle, bone, cartilage, nerve, blood vessel over fat. In research studies, individual supplements of the present compositions have demonstrated marked improvement of anti-oxidant function and the ability to down regulate inflammatory chemicals and genes responsible for contributing to the disease process. These effects have been demonstrated through extensive research, including clinical studies involving patients with various conditions. Individual components in the present compositions have demonstrated the ability to protect cells and promote chondrogenic differentiation of mesenchymal stem cells (MSCs).

EXAMPLES

An embodiment of a composition for providing joint support and mitigating one or more effects of arthritis comprises *Lactobacillus rhamnosus*, vitamin D, curcumin, *Boswellia* extract, and ginger. The composition is formulated as capsules, with a serving size of two capsules that contain ingredients or components as shown in the following TABLE 1.

TABLE 1

| Component | Amount per serving | % Daily value |
|---|---|---|
| Vitamin D3 (as cholecalciferol) | 1000 IU | 250% |
| Ginger Root Extract | 500 mg | n/a |
| *Boswellia Serrata* Gum Extract | 500 mg | n/a |
| Curcumin as Tumeric Root Extract | 350 mg | n/a |
| *Lactobacillus rhamnosus* | 10 billion CFU | n/a | n/a = Daily Value not established.
Other Ingredients: Hypromellose (Capsule), Rice Flour, Magnesium Stearate.

Adipogenesis Testing with the Composition of TABLE 1:

Human bone marrow-derived Mesenchymal stem cells (MSC) differentiation into adipocytes.

Frozen bone marrow mononuclear cells were purchased from Allcells (Allcells, Emeryville, Calif.). After thawing, mononuclear cells were resuspended in an α-minimal essential medium α-MEM, Invitrogen, Carlsbad Calif.) supplemented with 10% heat inactivated fetal bovine serum (FBS, Invitrogen, Carlsbad, Calif.) and 1% Antibiotics and Antimycotic (Invitrogen, Carlsbad, Calif.). The cells were plated at a density of 1-5×10$^6$ cells per 100 cm$^2$ dish. The cultures were maintained at 37° C. in a 5% CO$_2$ incubator and the medium was changed after 48 h and every 3~4 days thereafter. When the MSCs were confluent, the cells were recovered by the addition of 0.25% trypsin/EDTA (Invitrogen, Carlsbad, Calif.). MSCs (Passage 2-3) were plated in either a 75-cm$^2$ flask or a 24 well plate and cultured in α-MEM with 20% FBS up to a density of 2.0×10$^4$ cells/cm$^2$. The medium was replaced with adipogenic medium, and the cells were cultured for an additional 14 days. The adipogenic media consisted of complete culture medium supplemented with DMEM-high glucose, 10% (v/v) FBS, 10 μg/ml insulin, 0.5 mM dexamethasone (Sigma-Aldrich, St. Louis, Mo.), and 1% Antibiotics and Antimycotic (Invitrogen, Carlsbad, Calif.) in the presence and absence of the COX-1 inhibitor (2-Valeryloxybenzoic Acid, Cayman, Ann Arbor Mich.) and the COX-2 inhibitor (3-(4-methylsulphonylphenyl)-4-phenyl-5-trifluoromethylisoxazol, Cayman, Ann Arbor Mich.) with and without 20-HETE, 20-HETE agonist (20-5,14-HEDE) or 20-OH-PGE$_2$. 20-HETE, 20-HETE agonist or 20-OH-PGE$_2$ were added 3 times a week at concentrations of 0.1 and 1 μM. Inhibitors of COX-1 and COX-2 were added 3 times a week at a dose of 100 μM and 5 μM, respectively.

Oil Red O Staining.

At day 14 of adipogenesis, 0.21% Oil Red O in 100% isopropanol (Sigma-Aldrich, St. Louis, Mo.) was used. Briefly, adipocytes were fixed in 10% formaldehyde, washed in Oil-red O for 10 min, rinsed with 60% isopropanol (Sigma-Aldrich, St. Louis, Mo.), and the Oil red O eluted by adding 100% isopropanol for 10 min and OD measured at 490 nm, for 0.5 sec reading. MSC-derived adipocytes were measured by Oil red O staining (OD=490 nm) after day 14. Each values of Oil red O staining were normalized by cell numbers (Values at OD=490 nm).

In testing, it is observed that the formulation of TABLE 1 in the Oil Red O staining test resulted in a statistically significant decrease in adipogenesis relative to untreated human MSC. Additionally, testing has shown that without the presence of *Lactobacillus rhamnosus*, there was no statistically significant reduction in adipogenesis, even with the addition of the other ingredients of the formulation of TABLE 1. It is believed that the addition of *Lactobacillus rhamnosus* contributes to a synergistic effect in combination with the other ingredients, in a reduction of adipogenesis.

Anti-Oxidative Stress.

The percentage of live and dead cells was determined simultaneously by measuring intracellular esterase activity and plasma membrane integrity using the LIVE/DEAD® Viability/Cytotoxicity Assay Kit (Life Technologies). Briefly, human MSC were plated on 24 wells plate. On, next day cells were treated with ingredients and 100 μM $H_2O_2$ for 12 hr. The supernatant media from each well was collected into microtubes and cells were washed with 1×PBS, followed by collection of washes into respective microtubes to collect any floating or dead cells. The cells attached to the bottom of the plate were incubated in 1×PBS in a 37° C. incubator. The microtubes were centrifuged at 2000 rpm for 3 min to get the cell pellet. After removing supernatant, cell pellet was resuspended into 1×PBS containing 2 μM calcein AM and 4 μM ethidium/homodimer. Re-suspended cells were again poured into their respective wells and the plate was incubated at 37° C. for 15 min. The cells were then imaged under 10× objective using fluorescence microscope (Olympus IX71).

The anti-oxidative stress testing has shown that the other ingredients of the formulation of TABLE 1, when tested alone, did not result in a visually significant improvement in cell viability after the 12 hr exposure to $H_2O_2$. However, the formulation of TABLE 1 did result in a visually significant improvement in cell viability after the 12 hr exposure to $H_2O_2$. These test results further support the belief that the combination of the ingredients has a synergistic effect in protecting cells against oxidative stress and ultimate cell death.

It is also believed that the formulation of TABLE 1 will have a beneficial effect on chondrogenic and osteogenic differentiation of human MSC. Inflammation is detrimental to chondrogenesis and chondrocyte formation from human MSC. The formulation of TABLE 1 demonstrates anti-inflammatory effects, as inferred by the significant decrease in adipogenesis in the above-described experiments.

An embodiment of a composition for mitigating the effects of aging comprises *Lactobacillus rhamnosus*, *Boswellia* extract, ginger, green tea extract, and vitamin D. The composition is formulated as capsules, with a serving size of two capsules that contain ingredients or components as shown in the following TABLE 2.

TABLE 2

| Component | Amount per serving | % Daily value |
|---|---|---|
| Vitamin D (as cholecalciferol) | 1000 IU | 250% |
| Green Tea (leaf) Extract (*Camellia sinensis*) (standardized to 98% polyphenols, 80% catechins, and 50% EGCG) | 500 mg | n/a |
| *Boswellia Serrata* Extract (standardized to 65% boswellic acid) | 500 mg | n/a |
| Ginger root (from 8:1 concentrate) (*Zingiber officinale*) | 500 mg | n/a |
| *Lactobacillus rhamnosus* | 10 billion CFU | n/a | n/a = Daily Value not established.
Other Ingredients: Cellulose (Capsule), Inulin, Silicon Dioxide, Vegetable Magnesium Stearate.

Adipogenesis Testing with the Composition of TABLE 2:

Human bone marrow-derived MSCs differentiation into adipocytes.

Frozen bone marrow mononuclear cells were purchased from Allcells (Allcells, Emeryville, Calif.). After thawing, mononuclear cells were resuspended in an α-minimal essential medium α-MEM, Invitrogen, Carlsbad Calif.) supplemented with 10% heat inactivated fetal bovine serum (FBS, Invitrogen, Carlsbad, Calif.) and 1% Antibiotics and Antimycotic (Invitrogen, Carlsbad, Calif.). The cells were plated at a density of 1-5×10$^6$ cells per 100 cm$^2$ dish. The cultures were maintained at 37° C. in a 5% $CO_2$ incubator and the medium was changed after 48 h and every 3~4 days thereafter. When the MSCs were confluent, the cells were recovered by the addition of 0.25% trypsin/EDTA (Invitrogen, Carlsbad, Calif.). MSCs (Passage 2-3) were plated in either a 75-cm$^2$ flask or a 24 well plate and cultured in α-MEM with 20% FBS up to a density of 2.0×10$^4$ cells/cm$^2$. The medium was replaced with adipogenic medium, and the cells were cultured for an additional 14 days. The adipogenic media consisted of complete culture medium supplemented with DMEM-high glucose, 10% (v/v) FBS, 10 μg/ml insulin, 0.5 mM dexamethasone (Sigma-Aldrich, St. Louis, Mo.), and 1% Antibiotics and Antimycotic (Invitrogen, Carlsbad, Calif.) in the presence and absence of the COX-1 inhibitor (2-Valeryloxybenzoic Acid, Cayman, Ann Arbor Mich.) and the COX-2 inhibitor (3-(4-methylsulphonylphenyl)-4-phenyl-5-trifluoromethylisoxazol, Cayman, Ann Arbor Mich.) with and without 20-HETE, 20-HETE agonist (20-5,14-HEDE) or 20-OH-PGE$_2$. 20-HETE, 20-HETE agonist or 20-OH-PGE$_2$ were added 3 times a week at concentrations of 0.1 and 1 μM. Inhibitors of COX-1 and COX-2 were added 3 times a week at a dose of 100 μM and 5 μM, respectively.

Oil Red O Staining.

At day 14 of adipogenesis, 0.21% Oil Red O in 100% isopropanol (Sigma-Aldrich, St. Louis, Mo.) was used. Briefly, adipocytes were fixed in 10% formaldehyde, washed in Oil-red O for 10 min, rinsed with 60% isopropanol (Sigma-Aldrich, St. Louis, Mo.), and the Oil red O eluted by adding 100% isopropanol for 10 min and OD measured at 490 nm, for 0.5 sec reading. MSC-derived adipocytes were measured by Oil red O staining (OD=490 nm) after day 14. Each values of Oil red O staining were normalized by cell numbers (Values at OD=490 nm).

In testing, it is observed that the formulation of TABLE 2 in the Oil Red O staining test resulted in a statistically significant decrease in adipogenesis relative to untreated human MSC. Additionally, testing has shown that without the presence of *Lactobacillus rhamnosus*, there was no statistically significant reduction in adipogenesis, even with the addition of the other ingredients of the formulation of TABLE 2. It is believed that the addition of *Lactobacillus rhamnosus* contributes to a synergistic effect in combination with the other ingredients, in a reduction of adipogenesis.

Anti-Oxidative Stress.

The percentage of live and dead cells was determined simultaneously by measuring intracellular esterase activity and plasma membrane integrity using the LIVE/DEAD® Viability/Cytotoxicity Assay Kit (Life Technologies). Briefly, human MSC were plated on 24 wells plate. On, next day cells were treated with ingredients and 100 µM $H_2O_2$ for 12 hr. The supernatant media from each well was collected into microtubes and cells were washed with 1×PBS, followed by collection of washes into respective microtubes to collect any floating or dead cells. The cells attached to the bottom of the plate were incubated in 1×PBS in a 37° C. incubator. The microtubes were centrifuged at 2000 rpm for 3 min to get the cell pellet. After removing supernatant, cell pellet was resuspended into 1×PBS containing 2 µM calcein AM and 4 µM ethidium/homodimer. Re-suspended cells were again poured into their respective wells and the plate was incubated at 37° C. for 15 min. The cells were then imaged under 10× objective using fluorescence microscope (Olympus IX71).

The anti-oxidative stress testing has shown that the other ingredients of the formulation of TABLE 2, when tested alone, did not result in a visually significant improvement in cell viability after the 12 hr exposure to $H_2O_2$. However, the formulation of TABLE 2 did result in a visually significant improvement in cell viability after the 12 hr exposure to $H_2O_2$. These test results further support the belief that the combination of the ingredients has a synergistic effect in protecting cells against oxidative stress and ultimate cell death.

It is also believed that the formulation of TABLE 2 will have a beneficial effect on chondrogenic and osteogenic differentiation of human MSC. Inflammation is detrimental to chondrogenesis and chondrocyte formation from human MSC. The formulation of TABLE 2 demonstrates anti-inflammatory effects, as inferred by the significant decrease in adipogenesis in the above-described experiments.

An embodiment of a composition for mitigating issues arising from physical and athletic activities comprises *Lactobacillus rhamnosus*, curcumin, ginger, vitamin D, and *Epimedium* extract. The composition is formulated as capsules, with a serving size of two capsules that contain ingredients or components as shown in the following TABLE 3.

TABLE 3

| Component | Amount per serving | % Daily value |
|---|---|---|
| Vitamin D (as cholecalciferol) | 1000 IU | 250% |
| Curcumin | 350 mg | n/a |
| *Epidemium sagittatum* (standardized to 10% icariin) | 500 mg | n/a |
| Ginger root (from 8:1 concentrate) (*Zingiber officinale*) | 500 mg | n/a |
| *Lactobacillus rhamnosus* | 10 billion CFU | n/a | n/a = Daily Value not established.
Other Ingredients: Hypromellose (Capsule), Rice Flour, Magnesium Stearate.

Adipogenesis Testing with the Composition of TABLE 3:

Human bone marrow-derived MSCs differentiation into adipocytes.

Frozen bone marrow mononuclear cells were purchased from Allcells (Allcells, Emeryville, Calif.). After thawing, mononuclear cells were resuspended in an α-minimal essential medium α-MEM, Invitrogen, Carlsbad Calif.) supplemented with 10% heat inactivated fetal bovine serum (FBS, Invitrogen, Carlsbad, Calif.) and 1% Antibiotics and Antimycotic (Invitrogen, Carlsbad, Calif.). The cells were plated at a density of 1-5×10$^6$ cells per 100 cm$^2$ dish. The cultures were maintained at 37° C. in a 5% $CO_2$ incubator and the medium was changed after 48 h and every 3~4 days thereafter. When the MSCs were confluent, the cells were recovered by the addition of 0.25% trypsin/EDTA (Invitrogen, Carlsbad, Calif.). MSCs (Passage 2-3) were plated in either a 75-cm$^2$ flask or a 24 well plate and cultured in α-MEM with 20% FBS up to a density of 2.0×10$^4$ cells/cm$^2$. The medium was replaced with adipogenic medium, and the cells were cultured for an additional 14 days. The adipogenic media consisted of complete culture medium supplemented with DMEM-high glucose, 10% (v/v) FBS, 10 µg/ml insulin, 0.5 mM dexamethasone (Sigma-Aldrich, St. Louis, Mo.), and 1% Antibiotics and Antimycotic (Invitrogen, Carlsbad, Calif.) in the presence and absence of the COX-1 inhibitor (2-Valeryloxybenzoic Acid, Cayman, Ann Arbor Mich.) and the COX-2 inhibitor (3-(4-methylsulphonylphenyl)-4-phenyl-5-trifluoromethylisoxazol, Cayman, Ann Arbor Mich.) with and without 20-HETE, 20-HETE agonist (20-5,14-HEDE) or 20-OH-$PGE_2$. 20-HETE, 20-HETE agonist or 20-OH-$PGE_2$ were added 3 times a week at concentrations of 0.1 and 1 µM Inhibitors of COX-1 and COX-2 were added 3 times a week at a dose of 100 µM and 5 µM, respectively.

Oil Red O Staining.

At day 14 of adipogenesis, 0.21% Oil Red O in 100% isopropanol (Sigma-Aldrich, St. Louis, Mo.) was used. Briefly, adipocytes were fixed in 10% formaldehyde, washed in Oil-red O for 10 min, rinsed with 60% isopropanol (Sigma-Aldrich, St. Louis, Mo.), and the Oil red O eluted by adding 100% isopropanol for 10 min and OD measured at 490 nm, for 0.5 sec reading. MSC-derived adipocytes were measured by Oil red O staining (OD=490 nm) after day 14. Each values of Oil red O staining were normalized by cell numbers (Values at OD=490 nm).

In testing, it is observed that the formulation of TABLE 3 in the Oil Red O staining test resulted in a statistically significant decrease in adipogenesis relative to untreated human MSC. Additionally, testing has shown that without the presence of *Lactobacillus rhamnosus*, there was no statistically significant reduction in adipogenesis, even with the addition of the other ingredients of the formulation of TABLE 3. It is believed that the addition of *Lactobacillus rhamnosus* contributes to a synergistic effect in combination with the other ingredients, in a reduction of adipogenesis.

Anti-Oxidative Stress.

The percentage of live and dead cells was determined simultaneously by measuring intracellular esterase activity and plasma membrane integrity using the LIVE/DEAD® Viability/Cytotoxicity Assay Kit (Life Technologies). Briefly, human MSC were plated on 24 wells plate. On, next day cells were treated with ingredients and 100 µM $H_2O_2$ for 12 hr. The supernatant media from each well was collected into microtubes and cells were washed with 1×PBS, followed by collection of washes into respective microtubes to collect any floating or dead cells. The cells attached to the bottom of the plate were incubated in 1×PBS in a 37° C. incubator. The microtubes were centrifuged at 2000 rpm for 3 min to get the cell pellet. After removing supernatant, cell pellet was resuspended into 1×PBS containing 2 µM calcein AM and 4 µM ethidium/homodimer. Re-suspended cells were again poured into their respective wells and the plate was incubated at 37° C. for 15 min. The cells were then imaged under 10× objective using fluorescence microscope (Olympus IX71).

The anti-oxidative stress testing has shown that the other ingredients of the formulation of TABLE 3, when tested alone, did not result in a visually significant improvement in cell viability after the 12 hr exposure to $H_2O_2$, However, the formulation of TABLE 3 did result in a visually significant improvement in cell viability after the 12 hr exposure to $H_2O_2$. These test results further support the belief that the combination of the ingredients has a synergistic effect in protecting cells against oxidative stress and ultimate cell death.

It is also believed that the formulation of TABLE 3 will have a beneficial effect on chondrogenic and osteogenic differentiation of human MSC. Inflammation is detrimental to chondrogenesis and chondrocyte formation from human MSC. The formulation of TABLE 3 demonstrates anti-inflammatory effects, as inferred by the significant decrease in adipogenesis in the above-described experiments.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A dietary supplement including one of a tablet, a hypromellose capsule, and a cellulose capsule suitable for oral ingestion and containing a composition, the composition comprising a synergistic combination of:
   *Lactobacillus rhamnosus* in an amount from 100 million to 1 trillion CFU, ginger; and
   vitamin D.

2. The dietary supplement of claim 1, wherein the *Lactobacillus rhamnosus* comprises about 10 billion CFU of *Lactobacillus rhamnosus*.

3. The dietary supplement of claim 1, wherein the ginger comprises about 500 mg ginger.

4. The dietary supplement of claim 1, wherein the vitamin D comprises about 1,000 IU of vitamin D.

5. The dietary supplement of claim 1, further comprising curcumin.

6. The dietary supplement of claim 5, wherein the curcumin comprises about 350 mg tumeric root extract.

7. The dietary supplement of claim 1, further comprising *Boswellia* extract.

8. The dietary supplement of claim 7, wherein the *Boswellia* extract comprises about 500 mg *Boswellia serrata* extract.

9. The dietary supplement of claim 1, further comprising curcumin and *Boswellia* extract.

10. The dietary supplement of claim 1, further comprising green tea extract.

11. The dietary supplement of claim 10, wherein the green tea extract comprises about 500 mg of green tea leaf extract of *Camellia sinensis* standardized to about 98% polyphenols, 80% catechins, and 50% epigallocatechin gallate.

12. The dietary supplement of claim 1, further comprising *Boswellia* extract and green tea extract.

13. The dietary supplement of claim 1, further comprising *Epimedium* extract.

14. The dietary supplement of claim 13, wherein the *Epimedium* extract comprises about 500 mg of *Epimedium sagittatum* extract standardized to about 10% icariin.

15. The dietary supplement of claim 1, further comprising curcumin and *Epimedium* extract.

16. A method of aiding a health issue related to one of joint support, aging, and sports medicine comprising: administering a dietary supplement according to claim 1.

17. A method for providing joint support and mitigating an effect of arthritis comprising: administering a dietary supplement according to claim 9.

18. A method for mitigating an effect of aging comprising: administering a dietary supplement according to claim 12.

19. A method for mitigating an issue arising from one of a physical activity and an athletic activity comprising: administering a dietary supplement according to claim 15.

* * * * *